United States Patent [19]

Jimonet et al.

[11] Patent Number: 5,260,297

[45] Date of Patent: Nov. 9, 1993

[54] 2-IMINO-3-ALKYLBENZOTHIAZOLINE DERIVATIVES BEARING A HETEROCYCLIC SUBSTITUENT ON THE ALKYL GROUP, THEIR PREPARATION AND MEDICINAL PRODUCTS CONTAINING THEM.

[75] Inventors: Patrick Jimonet, Villepreux; Claude Gueremy, Houilles; Joseph Le Blevec, Colombes; Conception Nemecek, Choisy Le Roi, all of France

[73] Assignee: Rhone Poulenc Rorer, S.A., Antony Cedex, France

[21] Appl. No.: 815,220

[22] Filed: Dec. 31, 1991

Related U.S. Application Data

[63] Continuation-in-part of Ser. No. 550,014, Jul. 9, 1990, abandoned.

[51] Int. Cl.$^5$ .............. C07D 417/06; A61K 31/495; A61K 31/44; A61K 31/445
[52] U.S. Cl. .................... 514/255; 514/323; 514/338; 544/295; 544/364; 544/368; 546/198; 546/270
[58] Field of Search .............. 546/198, 270; 544/368, 544/364, 295; 514/255, 323, 338

[56] References Cited

U.S. PATENT DOCUMENTS

| | | | |
|---|---|---|---|
| 4,113,732 | 9/1978 | Opgenorth | 26/305 |
| 4,370,338 | 1/1983 | Mizoule | 424/270 |
| 4,980,356 | 12/1990 | Audiau | 514/269 |
| 5,008,280 | 4/1991 | Gueremy | 514/367 |

Primary Examiner—Robert Gerstl
Attorney, Agent, or Firm—Morgan & Finnegan

[57] ABSTRACT

Compounds of formula:

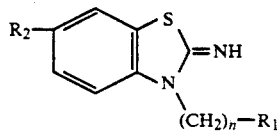

in which $R_1$ represents a substituted 1-piperazinyl, substituted 1,2,3,6-tetrahydro-1-pyridyl or substituted piperidino radical, $R_2$ represents a polyfluoroalkoxy or a polyfluoroalkyl radical and n is equal to 2 or 3, the salts of these compounds with an acid, processes for preparing them and medicinal products containing them.

9 Claims, No Drawings

2-IMINO-3-ALKYLBENZOTHIAZOLINE DERIVATIVES BEARING A HETEROCYCLIC SUBSTITUENT ON THE ALKYL GROUP, THEIR PREPARATION AND MEDICINAL PRODUCTS CONTAINING THEM.

This application is a continuation-in-part application of U.S. application Ser. No. 07/550,014 filed, Jul. 9, 1990, now abandoned hereby incorporated by reference.

The present invention relates to compounds of formula:

(I)

to their salts, to processes for preparing them and to medicinal products containing them.

In the formula (I), $R_1$ represents
- a 1-piperazinyl radical substituted at the 4-position with (a) a phenyl radical, (b) a phenyl radical substituted with at least one substituent selected from halogen atoms and alkyl and alkoxy radicals, (c) a phenylalkyl radical, (d) a pyridyl radical or (e) a pyrimidinyl radical,
- a 1,2,3,6-tetrahydro-1-pyridyl radical substituted at the 4-position with a phenyl radical or a phenyl radical substituted with at least one substituent selected from halogen atoms and alkyl and alkoxy radicals,
- a piperidino radical substituted at the 4-position with a phenyl radical or a phenyl radical substituted with at least one substituent selected from halogen atoms and alkyl and alkoxy radicals, $R_2$ represents a polyfluoroalkoxy or polyfluoroalkyl radical, and n is equal to 2 to 3.

In the definitions above and those to be mentioned below, the alkyl and alkoxy radicals and alkyl and alkoxy portions contain 1 to 4 carbon atoms in a straight or branched chain.

The polyfluoroalkoxy and polyfluoroalkyl radicals are preferably trifluoromethoxy, pentafluoroethoxy, 2,2,2-trifluoroethoxy, 1,1,2,2-tetrafluoroethoxy or trifluoromethyl radicals.

The halogen atoms are preferably fluorine, chlorine or bromine atoms.

The invention also relates to the addition salts of the compounds of formula (I) with inorganic or organic acids.

The compounds of formula (I) may be prepared by the hydrolysis of a derivative of formula:

(II)

in which $R_1$, $R_2$ and n have the same meanings as in the formula (I).

This hydrolysis is generally performed by means of a base such as an alkali metal carbonate (preferably sodium or potassium carbonate) or concentrated ammonia solution, in a water/alcohol mixture, at a temperature in the region of 20° C.

The derivatives of formula (II) may be obtained by the action of a derivative of formula:

(III)

in which $R_2$ and n have the same meanings as in the formula (I) and $R_3$ represents a reactive group such as a methanesulphonyl or p-toluenesulphonyl radical, on an amine of formula:

$HR_1$ (IV)

in which $R_1$ has the same meanings as in the formula (I).

This reaction is generally performed in an inert solvent such as an aromatic solvent (e.g. benzene, toluene, xylene) or dimethylformamide, at a temperature between 20° C. and the boiling point of the solvent.

The derivatives of formula (III) may be prepared by the action of a derivative of formula:

(V)

in which $R_2$ and n have the same meanings as in the formula (I), on methanesulphonyl or p-toluenesulphonyl chloride, either in an inert solvent such as an aromatic solvent (e.g. benzene, toluene, xylene) or a chlorinated solvent (e.g. chloroform, methylene chloride), in the presence of a tertiary amine such as triethylamine, at a temperature in the region of 20° C., or in pyridine, at a temperature in the region of 0° C.

The derivatives of formula (V) may be obtained by the action of ethyl trifluoroacetate on a derivative of formula:

(VI)

in which $R_2$ and n have the same meanings as in the formula (I).

This reaction is generally performed in an alcohol (e.g. methanol, ethanol), in the presence of a tertiary base such as triethylamine, at a temperature in the region of 20° C.

The derivatives of formula (VI) may be prepared by the action of a halogenated derivative of formula:

$Hal-(CH_2)_n-OH$ (VII)

in which n has the same meanings as in the formula (I) and Hal represents a halogen atom (preferably bromine or chlorine) on a 2-amino-6-polyfluoroalkoxybenzothiazole or a 2-amino-6-polyfluoroalkylbenzothiazole.

This reaction is performed in an alcohol (preferably ethanol or methanol), at the boiling point of the solvent.

2-Amino-6-polyfluoroalkoxybenzothiazoles and 2-amino-6-polyfluoroalkylbenzothiazoles may be prepared by application or adaptation of the method described by L. M. YAGUPOL'SKII et al., Zh. Obsch. Khim., 33(7), 2301, (1963) and in U.S. Pat. No. 2,822,359.

The compounds of formula (I) may also be prepared by the action of bromine and an alkali metal thiocyanate on a derivative of formula:

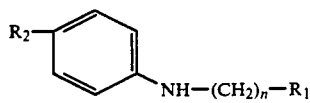

(VIII)

in which $R_1$, $R_2$ and n have the same meanings as in the formula (I).

This reaction is preferably performed in acetic acid, at a temperature in the region of 20° C.

As an alkali metal thiocyanate, potassium thiocyanate is preferably used.

The derivatives of formula (VIII) may be obtained by the action of an amine of formula (IV) on a derivative of formula:

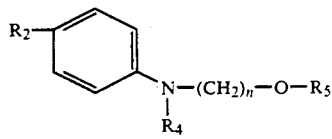

(IX)

in which $R_2$ and n have the same meanings as in the formula (I) and $R_4$ and $R_5$ represent a p-toluenesulphonyl radical.

This reaction is preferably performed in the presence of sodium hydrogen carbonate, in an inert solvent such as dimethylformamide, at a temperature of between 50° C. and 100° C.

The derivatives of formula (IX) may be obtained by the action of p-toluenesulphonyl chloride on a derivative of formula:

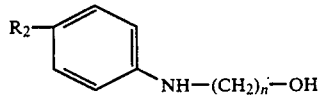

(X)

in which $R_2$ and n have the same meanings as in the formula (I).

This reaction is generally performed in an inert solvent such as a chlorinated solvent (e.g. chloroform, methylene chloride), at a temperature of between 0° C. and 30° C.

The derivatives of formula (X) may be obtained by the action of a 4-polyfluoroalkoxyaniline or a 4-polyfluoroalkylaniline on a derivative of formula (VII).

This reaction is generally performed at a temperature of between 100° C. and 170° C.

The reaction mixtures obtained by the various processes described above are treated according to conventional physical methods (evaporation, extraction, distillation, crystallization, chromatography, etc.) or chemical methods (salt formation, etc.).

The compounds of formula (I), in free base form, can be optionally converted to addition salts with an inorganic or organic acid by the action of such an acid in an organic solvent such as an alcohol, ketone, ether or chlorinated solvent.

The compounds of formula (I) and their salts possess advantageous pharmacological properties. These compounds are active with respect to glutamate-induced convulsions, and are hence useful in the treatment and prevention of convulsive phenomena, schizophrenic disorders, and in particular the deficiency forms of schizophrenia, sleep disorders, phenomena linked to cerebral ischaemia and also neurological conditions in which glutamate may be implicated, such as Alzheimer's disease, Huntington's chorea, amyotrophic lateral sclerosis and olivopontocerebella atrophy.

The activity of the compounds of formula (I) with respect to glutamate-induced convulsions was determined according to a technique based on that of I. P. LAPIN, J. Neural. Transmission, vol. 54, 229–238, (1982); intracerebroventricular injection of glutamate being performed according to a technique based on that of R. CHERMAT and P. SIMON, J. Pharmacol. (Paris), vol. 6, 489–492 (1975). Their $ED_{50}$ is generally equal to or less than 10 mg/kg.

The compounds of formula (I) possess low toxicity. Their $LD_{50}$ is more than 15 mg/kg when administered I.P. in mice.

For medicinal use, the compounds of formula (I) may be employed as they are, or in the state of pharmaceutically acceptable salts, i.e. salts which are non-toxic at the doses at which they are used.

As examples of pharmaceutically acceptable salts, the addition salts with inorganic or organic acids, such as acetate, propionate, succinate, benzoate, fumarate, maleate, oxalate, methanesulphonate, isethionate, theophylline acetate, salicylate, phenolphthalinate, methylenebis($\beta$-hydroxynaphthoate), hydrochloride, sulphate, nitrate and phosphate, may be mentioned.

The examples which follow, given without implied limitation, show how the invention may be put into practice.

EXAMPLE 1

3-{2-[4-(2-Pyridyl)-1-piperzinyl]ethyl}-2-trifluoroacetylimino-6-trifluoromethoxybenzothiazoline (1.3 g), dissolved in a mixture of 7% strength aqueous potassium carbonate solution (19 cc) and methanol (32 cc), is stirred at a temperature in the region of 20° C. for 4 hours. The medium is concentrated under reduced pressure (20 mmHg; 2.7 kPa) and the residue is taken up with distilled water (300 cc). The aqueous phase is extracted with ethyl ether (3×200 cc), dried over magnesium sulphate and concentrated to dryness under reduced pressure. The residue obtained is purified by chromatography on a silica column with acetone as eluent. After formation of the trihydrochloride by adding 4.2N ethereal hydrogen chloride in acetone, 2-imino-3-{2-[4-(2-pyridyl)-1-piperazinyl]ethyl}-6-trifluoromethoxybenzothiazoline trihydrochloride (0.73 g), m.p. about 230° C., is obtained.

3-{2-[4-(2-Pyridyl)-1-piperazinyl]ethyl}-2-trifluoroacetylimino-6-trifluoromethoxybenzothiazoline may be prepared according to the following process: a mixture of 2-(2-trifluoroacetylimino-6-trifluoromethoxy-3-benzothiazolinyl)ethyl methanesulphonate (4.52 g) in toluene (100 cc) and 4-(2-pyridyl)piperazine (6.9 g) is heated to reflux for 2 hours, cooled to 4° C. and then drained. The toluene filtrate is evaporated under reduced pressure and purified by chromatography on a silica column with dichloromethane as eluent. 3-{2-[4-(2-Pyridyl)-1-piperazinyl]ethyl}-2-trifluoroacetylimino-6-trifluoromethoxybenzothiazoline (1.3 g), m.p. 132° C., is obtained.

2-(2-Trifluoroacetylimino-6-trifluoromethoxy-3-benzothiazolinyl)ethyl methanesulphonate may be prepared in the following manner: triethylamine (6.9 g) is added gradually to a mixture of methylene chloride (120 cc), methanesulphonyl chloride (7.34 g) and 2-(2-trifluoroacetylimino-6-trifluoromethoxy-3-benzothiazolinyl)ethanol (12 g). After 1 hour's stirring at a temperature in the region of 20° C., the reaction medium is cooled to 10° C., drained, washed with cold methylene chloride (20 cc) and then dried at 40° C. under reduced pressure. 2-(2-Trifluoroacetylimino-6-trifluoromethoxy-3-benzothiazolinyl)ethyl methanesulphonate (10 g), m.p. 145° C., is obtained. A 2nd crop (2.7 g) is obtained by washing the filtrate with water (100 cc), drying over magnesium sulphate, concentration to a residual volume of approximately 50 cc, cooling to 5° C. and then draining.

2-(2-Trifluoroacetylimino-6-trifluoromethoxy-3-benzothiazolinyl)ethanol may be prepared in the following manner: 2-(2-imino-6-trifluoromethoxy-3-benzothiazolinyl)ethanol hydrobromide (20.7 g), ethyl trifluoroacetate (9.8 g) and triethylamine (16.1 cc) are stirred in ethanol (100 cc) for 22 hours at a temperature in the region of 20° C. After concentration to dryness under reduced pressure, the residue obtained is purified by chromatography on a silica column with ethyl acetate as eluent. 2-(2-Trifluoroacetylimino-6-trifluoromethoxy-3-benzothiazolinyl)ethanol (19.2 g), m.p. 144° C., is obtained.

2-(2-Imino-6-trifluoromethoxy-3-benzothiazolinyl)ethanol may be prepared according to the following process: 2-amino-6-trifluoromethoxybenzothiazole (9.4 g) and 2-bromoethanol (10 g) in absolute ethanol (30 cc) are heated to boiling for 95 hours. The mixture is then cooled to a temperature in the region of 20° C. The precipitate formed is filtered off and washed with ethyl ether (100 cc). 2-(2-Imino-6-trifluoromethoxy-3-benzothiazolinyl)ethanol hydrobromide (6.4 g), m.p. 219° C., is obtained.

2-Amino-6-trifluoromethoxybenzothiazole may be prepared according to the method described by L. M. YAGUPOL'SKII et al., Zh. Obshch. Khim, 33(7), 2301 (1963).

EXAMPLE 2

Using the procedure described in Example 1, but starting with 3-{2-[4-(4-methylphenyl)-1-piperazinyl]ethyl}-2-trifluoroacetylimino-6-trifluoromethoxybenzothiazoline (0.9 g) in methanol (18 cc) and a 7% strength aqueous-alcoholic solution (14 cc) of potassium carbonate, 2-imino-3-{2-[4-(4-methylphenyl)-1-piperazinyl]ethyl}-6-trifluoromethoxybenzothiazoline (0.7 g), m.p. 120° C., is obtained.

3-{2-[4-(4-Methylphenyl)-1-piperazinyl]ethyl}-2-trifluoroacetylimino-6-trifluoromethoxybenzothiazoline may be prepared in the following manner: the procedure is as in Example 1, starting with 2-(2-trifluoroacetylimino-6-trifluoromethoxy-3-benzothiazolinyl)ethyl methanesulphonate (4.52 g) in toluene (150 cc) and 4-(4-methylphenyl)piperazine (5.29 g). After purification by chromatography on a silica column with a mixture of dichloromethane and ethyl acetate (98:2 by volume) as eluent, 3-{-2-[4-(4-methylphenyl)-1-piperazinyl]ethyl}-2-trifluoroacetylimino-6-trifluoromethoxy-benzothiazoline (0.9 g) is obtained.

EXAMPLE 3

Using the procedure described in Example 1, starting with 2-(2-trifluoroacetylimino-6-trifluoromethoxy-3-benzothiazolinyl)ethyl methanesulphonate (5.88 g) in toluene (200 cc) and 4-(2-methylphenyl)piperazine (6.87 g) and after 2 hours under reflux, the toluene filtrate is evaporated under reduced pressure. To the residue thereby obtained, methanol (100 cc) and a 7% strength aqueous-alcoholic solution (20 cc) of potassium carbonate are added and the mixture is stirred for 2 hours at approximately 20° C. The alcohol is evaporated off under reduced pressure and the residue is purified by chromatography on a silica column with a dichloromethane/ethyl acetate mixture (70:30 by volume) as eluent, and then an ethyl acetate/cyclohexane mixture (50:50 by volume) as eluent. 2-Imino-3-{2-[4-(2-methylphenyl)-1-piperazinyl]ethyl}-6-trifluoromethoxybenzothiazoline (1.8 g), m.p. 135° C., is thereby obtained.

EXAMPLE 4

Using the procedure described in Example 1, but starting with 3-[2-(4-benzyl-1-piperazinyl)ethyl]-2-trifluoroacetylimino-6-trifluoromethoxybenzothiazoline (3.8 g) in methanol (20 cc) and a 7% strength aqueous-alcoholic solution (10 cc) of potassium carbonate, and after purification by chromatography on a silica column with an ethyl acetate/cyclohexane mixture (50:50 by volume) as eluent, followed by the addition of 4.2N ethereal hydrogen chloride, 3-[2-(4-benzyl-1-piperazinyl)ethyl]-2-imino-6-trifluoromethoxybenzothiazoline hydrochloride (2.5 g), m.p. about 230° C., is obtained.

3-[2-(4-Benzyl-1-piperazinyl)ethyl]-2-trifluoroacetylimino-6-trifluoromethoxybenzothiazoline may be prepared in the following manner: the procedure is as in Example 1, starting with 2-(2-trifluoroacetylimino-6-trifluoromethoxy-3-benzothiazolinyl)ethyl methanesulphonate (4.52 g) in toluene (120 cc) and 4-benzylpiperazine (7 g). After purification by chromatography on a silica column with a dichloromethane/ethyl acetate mixture (50:50 by volume) as eluent, 3-[2-(4-benzyl-1-piperazinyl)ethyl]-2-trifluoroacetylimino-6-trifluoromethoxybenzothiazoline (3.8 g), is obtained.

EXAMPLE 5

Using the procedure described in Example 1, starting with 2-(2-trifluoroacetylimino-6-trifluoromethoxy-3-benzothiazolinyl)ethyl methanesulphonate (4.52 g) in toluene (150 cc) and 2-4-(2-pyrimidinyl)piperazine (6.5 g) and after 4 hours under reflux, the toluene filtrate is evaporated under reduced pressure. Methanol (100 cc) and a 7% strength aqueous-alcoholic solution (20 cc) of potassium carbonate are added to the toluene residue. After 2 hours' stirring at approximately 20° C., the methanol is evaporated off under reduced pressure and the residue is purified by chromatography on a silica column with a dichloromethane/methanol mixture (90:10 by volume) as eluent. After formation of the trihydrochloride by adding 4.2N ethereal hydrogen chloride, 2-imino-3-{2-[4-(2-pyrimidinyl)-1-piperazinyl- ]ethyl}-6-trifluoromethoxybenzothiazoline trihydrochloride (1.13 g), m.p. about 270° C., is obtained.

EXAMPLE 6

3-[3-(4-Phenyl-1-piperazinyl)propyl]-2-trifluoroacetylimino-6-trifluoromethoxybenzothiazoline hydrochloride (3.6 g), dissolved in a mixture of 7% strength aqueous potassium carbonate solution (45 cc) and methanol (150 cc), is stirred for 4 hours at a temperature in the region of 20° C. After concentration to dryness, the reaction medium is taken up in distilled water (100 cc) and the organic phase extracted with ethyl acetate (2×100 cc), dried over magnesium sulphate and concentrated to dryness under reduced pressure (20 mmHg; 2.7 kPa). After formation of the dihydrochloride by adding 4.2N ethereal hydrogen chloride (4 cc) in ethyl acetate, the precipitate is recrystallized in an absolute ethanol/ethyl ether mixture (50:50 by volume). 2-Imino-3-[3-(4-phenyl-1-piperazinyl)propyl]-6-trifluoromethoxybenzothiazoline dihydrochloride (1.6 g), m.p. 260° C., is obtained.

3-[3-(4-Phenyl-1-piperazinyl)propyl]-2-trifluoroacetylimino-6-trifluoromethoxybenzothiazoline hydrochloride may be prepared according to the following process: 3-(2-trifluoroacetylimino-6-trifluoromethoxy-3-benzothiazolinyl)propyl p-toluenesulphonate (4.4 g), N-phenylpiperazine (1.44 g) and sodium hydrogen carbonate (0.68 g) in dimethylformamide (50 cc) are heated to 80° C. for 19 hours. The reaction medium is concentrated to dryness under reduced pressure (7 mmHg; 0.95 kPa), the residue taken up in distilled water (100 cc) and the organic phase extracted with dichloromethane (50 cc). After drying over magnesium sulphate and concentration to dryness under reduced pressure, the oily residue obtained is taken up with 1N aqueous hydrochloric acid (15 cc) and the hydrochloride formed precipitated in distilled water (15 cc). 3-[3-(4-Phenyl-1-piperazinyl)propyl]-2-trifluoroacetylimino-6-trifluoromethoxybenzothiazoline hydrochloride (4 g), m.p. 238° C., is obtained.

3-(2-Trifluoroacetylimino-6-trifluoromethoxy-3-benzothiazolinyl)propyl p-toluenesulphonate may be prepared according to the following process: 3-(2-trifluoroacetylimino-6-trifluoromethoxy-3-benzothiazolinyl)propanol (11 g) is added gradually to p-toluenesulphonyl chloride (10.8 g) dissolved in pyridine (200 cc) cooled to 0° C. The reaction is continued for 1 hour at 5° C. and the reaction medium is then kept in the cold (6°-7° C.) for 15 hours. After addition to distilled water (2 liters), extraction with ethyl acetate (200 cc), washing with 1N hydrochloric acid (2×50 cc), drying over magnesium sulphate and concentration to dryness under reduced pressure, 3-(2-trifluoroacetylimino-6-trifluoromethoxy-3-benzothiazolinyl)propyl p-toluenesulphonate (6.7 g), m.p. 139° C., is obtained.

3-(2-Trifluoroacetylimino-6-trifluoromethoxy-3-benzothiazolinyl)propanol may be prepared in the following manner: 3-(2-imino-6-trifluoromethoxy-3-benzothiazolinyl)propanol (24.8 g), ethyl trifluoroacetate (14.2 g) and triethylamine (8.6 g) are stirred in absolute ethanol (250 cc) for 24 hours at a temperature in the region of 20° C. The reaction medium is then cooled to 0°-5° C. and the precipitate formed filtered off and dried. 3-(2-Trifluoroacetylimino-6-trifluoromethoxy-3-benzothiazolinyl)propanol (28.2 g), m.p. 144° C., is obtained.

3-(2-Imino-6-trifluoromethoxy-3-benzothiazolinyl)propanol may be prepared according to the following process: 2-amino-6-trifluoromethoxybenzothiazole (82 g) and 3-bromopropanol (65 cc) in absolute ethanol (25 cc) are heated to boiling for 72 hours. The mixture is then cooled to a temperature in the region of 20° C. The oil obtained is taken up in distilled water (1 liter) and the organic phase extracted with dichloromethane (3×200 cc). After drying over magnesium sulphate and concentration to dryness under reduced pressure, the crude product is purified by chromatography on a silica column with ethyl acetate as eluent. 3-(2-Imino-6-trifluoromethoxy-3-benzothiazolinyl)propanol (25 g), m.p. 106° C., is obtained.

EXAMPLE 7

Using the procedure described in Example 1, starting with 3-{2-[4-(m-tolyl)-1-piperazinyl]ethyl}-2-trifluoroacetylimino-6-trifluoromethoxybenzothiazoline (1 g) in methanol (30 cc) and a 7% strength aqueous-alcoholic solution (15 cc) of potassium carbonate, and after purification by chromatography on a silica column with an ethyl acetate/cyclohexane mixture (50:50 by volume) as eluent, followed by the addition of 4.2N ethereal hydrogen chloride, 2-imino-3-{2-[4-(m-tolyl)-1-piperazinyl]ethyl}-6-trifluoromethoxybenzothiazoline hydrochloride (0.6 g), m.p. about 250° C., is obtained.

3-{2-[4-(m-Tolyl)-1-piperazinyl)ethyl}-2-trifluoroacetylimino-6-trifluoromethoxybenzothiazoline may be prepared in the following manner: the procedure is as in Example 1, starting with 2-(2-trifluoroacetylimino-6-trifluoromethoxy-3-benzothiazolinyl)ethyl methanesulphonate (4.52 g) in toluene (150 cc) and 4-(3-methylphenyl)piperazine (5.29 g). After purification by chromatography on a silica column with a dichloromethane/ethyl acetate mixture (70:30 by volume) as eluent, 3-{2-[4-(m-tolyl)-1-piperazinyl]ethyl}-2-trifluoroacetylimino-6-trifluoromethoxybenzothiazoline (1 g) is obtained.

EXAMPLE 8

Bromine (1.15 g), dissolved in acetic acid (15 cc), is added dropwise at a temperature in the region of 20° C. to a mixture of 4-phenyl-1-[2-(4-trifluoromethoxyanilino)ethyl]-1,2,3,6-tetrahydropyridine (2.62 g) and potassium thiocyanate (2.8 g) in acetic acid (50 cc). After the usual treatment, 2-imino-3-[2-(4-phenyl-1,2,3,6-tetrahydro-1-pyridyl)ethyl]-6-trifluoromethoxybenzothiazoline dihydrochloride (0.67 g), m.p. 256° C., is obtained.

4-Phenyl-1-[2-(4-trifluoromethoxyanilino)ethyl]-1,2,3,6-tetrahydropyridine may be prepared in the following manner: a mixture of N-(p-toluenesulphonyl)-2-(4-trifluoromethoxyanilino)ethyl p-toluenesulphonate (5.56 g), 4-phenyl-1,2,3,6-tetrahydropyridine (1.84 g) and sodium hydrogen carbonate (0.97 g) in dimethylformamide (95 cc) is heated to 80° C. for 18 hours. After the usual treatment, 4-phenyl-1-[2-(4-trifluoromethoxyanilino)ethyl]-1,2,3,6-tetrahydropyridine (2.62 g) is obtained in the form of an oil, which is used without further treatment in the subsequent syntheses.

N-(p-Toluenesulphonyl)-2-(4-trifluoromethoxyanilino)ethyl p-toluenesulphonate may be prepared according to the following process: p-toluenesulphonyl chloride (8.6 g) is added gradually to 2-(4-trifluoromethoxyanilino)ethanol (5.0 g) and triethylamine (6.35 cc) in dichloromethane (50 cc) at 0° C. Reaction is continued for 2 hours at a temperature in the region of 20° C., the reaction medium then washed with distilled water (3×50 cc) and the organic phase dried over magnesium sulphate and concentrated to dryness under reduced pressure (20 mmHg; 2.7 kPa). After the addition of absolute ethanol (50 cc), the precipitate formed is filtered off. N-(p-Toluenesulphonyl)-2-(4-trifluoromethoxyanilino)ethyl p-toluenesulphonate (7.3 g), m.p. 88° C., is obtained.

2-(4-Trifluoromethoxyanilino)ethanol may be prepared in the following manner: 4-trifluoromethoxyaniline (88.5 g) and 2-bromoethanol (31.2 g) are heated to 160° C. for 1.5 hours. After cooling to a temperature in the region of 20° C., the reaction medium is taken up in dichloromethane (200 cc), the insoluble matter filtered off and the filtrate concentrated to dryness under reduced pressure. After purification by chromatography on a silica column with an ethyl acetate/cyclohexane mixture (40:60 by volume) as eluent, 2-(4-trifluoromethoxyanilino)ethanol (26.8 g) is obtained in the form of an orange-colored oil.

EXAMPLE 9

3-[2-(4-Phenylpiperazinyl)ethyl]-2-trifluoroacetylimino-6-trifluoromethoxybenzothiazoline hydrochloride (1.1 g), dissolved in a mixture of 7% strength aqueous potassium carbonate solution (5 cc) and methanol (100 cc), are stirred at a temperature in the region of 20° C. for 5 hours. The reaction medium is added to distilled water (200 cc) and the organic phase extracted with ethyl ether (3×150 cc), dried over magnesium sulphate and concentrated to dryness under reduced pressure (20 mmHg; 2.7 kPa). After formation of the hydrochloride by adding 4.2N ethereal hydrogen chloride (0.45 cc) in ethyl acetate (30 cc), 2-imino-3-[2-(4-phenylpiperazinyl)ethyl]-6-trifluoromethoxybenzothiazoline hydrochloride (0.8 g), m.p. 230° C., is obtained.

3-[2-(4-Phenylpiperazinyl)ethyl]-2-trifluoroacetylimino-6-trifluoromethoxybenzothiazoline hydrochloride may be prepared according to the following process: 2-(2-trifluoroacetylimino-6-trifluoromethoxy-3-benzothiazolinyl)ethyl p-toluenesulphonate (6.5 g), N-phenylpiperazine (2.2 g) and sodium bicarbonate (1.0 g) in dimethylformamide (80 cc) are heated to 60° C. for 19 hours. The reaction medium is added to distilled water (300 cc) and the organic phase is extracted with dichloromethane (3×50 cc). After drying over magnesium sulphate and concentration to dryness under reduced pressure, the oily residue obtained is taken up with 1N hydrochloric acid (20 cc) and the hydrochloride formed precipitated in ethanol (20 cc). 3-[2-(4-phenylpiperazinyl)ethyl]-2-trifluoroacetylimino-6-trifluoromethoxybenzothiazoline hydrochloride (1.1 g), m.p. 204° C., is obtained.

2-(2-Trifluoroacetylimino-6-trifluoromethoxy-3-benzothiazolinyl)ethyl p-toluenesulphonate may be prepared according to the following process: 2-(2-trifluoroacetylimino-6-trifluoromethoxy-3-benzothiazolinyl)ethanol (19.3 g) is added gradually to p-toluenesulphonyl chloride (19.7 g) dissolved in pyridine (120 cc) cooled to 0° C. Reaction is continued for 1 hour at 10°–15° C. The reaction medium is added to distilled water (500 cc) and the organic phase extracted with dichloromethane (3×100 cc). After washing with 1N hydrochloric acid (2×50 cc) and then distilled water (2×50 cc), drying over magnesium sulphate and concentration to dryness under reduced pressure (20 mmHg; 2.7 kPa), 2-(2-trifluoroacetylimino-6-trifluoromethoxy-3-benzothiazolinyl)ethanol p-toluenesulphonate (14.1 g), m.p. 143° C., is obtained.

2-(2-Trifluoroacetylimino-6-trifluoromethoxy-3-benzothiazolinyl)ethanol may be prepared in the following manner: 2-(2-imino-6-trifluoromethoxy-3-benzothiazolinyl)ethanol hydrobromide (20.7 g), ethyl trifluoroacetate (9.8 g) and triethylamine (16.1 cc) are stirred in ethanol (100 cc) for 22 hours at a temperature in the region of 20° C. After concentration to dryness under reduced pressure, the residue obtained is purified by chromatography on a silica column with ethyl acetate as eluent. 2-(2-Trifluoroacetylimino-6-trifluoromethoxy-3-benzothiazolinyl)ethanol (19.2 g), m.p. 144° C., is obtained.

2-(2-Imino-6-trifluoromethoxy-3-benzothiazolinyl)ethanol may be prepared according to the following process: 2-amino-6-trifluoromethoxybenzothiazole (9.4 g) and 2-bromoethanol (10 g) in absolute ethanol (30 cc) are heated to boiling for 95 hours. The mixture is then cooled to a temperature in the region of 20° C. The precipitate formed is filtered off and washed with ethyl ether (100 cc). 2-(2-Imino-6-trifluoromethoxy-3-benzothiazolinyl)ethanol hydrobromide (6.4 g), m.p. 219° C., is obtained.

2-Amino-6-trifluoromethoxybenzothiazole may be prepared according to the method described by L. M. YAGUPOL'SHII et al., Zh. Obshch. Khim, 33(7), 2301 (1963).

EXAMPLE 10

3-{2-[4-(4-Methoxyphenyl)-1-piperazinyl]ethyl}-2-trifluoroacetylimino-6-trifluoromethoxybenzothiazoline hydrochloride (1.53 g), methanol (33 cc) and 7% strength potassium carbonate solution (21 cc) in a mixture of methanol (2 volumes) and water (5 volumes) are stirred for 4 hours at a temperature in the region of 20° C. The reaction medium is concentrated under reduced pressure and then extracted with ethereal sulphuric acid. The organic phase is dried over magnesium sulphate and then treated with an excess of alcoholic hydrochloric acid solution. The precipitate is drained, washed with ethereal sulphuric acid and dried at 50° C. at 20 mmHg. 2-Imino-3-{2-[4-(4-methoxyphenyl)-1-piperazinyl]ethyl}-6-trifluoromethoxybenzothiazoline trihydrochloride (1.05 g), m.p. 240° C., is obtained.

3-{2-[4-(4-Methoxyphenyl)-1-piperazinyl]ethyl-2-trifluoroacetylimino-6-trifluoromethoxybenzothiazoline hydrochloride may be prepared in the following manner: a mixture of 2-(2-trifluoroacetylimino-6-trifluoromethoxy-3-benzothiazolinyl)ethyl methanesulphonate (4.52 g), toluene (120 cc) and the base liberated from 4-(p-methoxyphenyl)piperazine dihydrochloride (10.56 g) is heated to reflux for 1 hour, cooled to +4° C. and then drained. The toluene filtrate is evaporated under reduced pressure and then treated with 1.2N aqueous hydrochloric acid solution (45 cc). The hydrochloride separates in amorphous form and then crystallizes on grinding with ethanol (50 cc). After draining, washing with ethanol (15 cc) and drying at 50° C. at 20 mmHg, 3-{2-[4-(4-methoxyphenyl)-1-piperazinyl]ethyl}-2-trifluoroacetylimino-6-trifluoromethoxybenzothiazoline hydrochloride (1.7 g) is obtained.

2-(2-Trifluoroacetylimino-6-trifluoromethoxy-3-benzothiazolinyl)ethyl methanesulphonate may be prepared in the following manner: triethylamine (6.9 g) is added gradually to a mixture of methylene chloride (120 cc), methanesulphonyl chloride (7.34 g) and 2-(2-trifluoroacetylimino-6-trifluoromethoxy-3-benzothiazolinyl) ethanol (12 g). After 1 hour's stirring at a temperature in the region of 20° C., the reaction medium is cooled to 10° C., drained, washed with cold methylene chloride (20 cc) and then dried at 40° C. under reduced pressure. 2-(2-Trifluoroacetylimino-6-trifluoromethoxy-3-benzothiazolinyl)ethyl methanesulphonate (10 g), m.p. 145° C., is obtained. A 2nd crop (2.7 g) is obtained by washing the filtrate with water (100 cc), drying over magnesium sulphate, concentration to a residual volume of approximately 50 cc, cooling to 5° C. and then draining.

EXAMPLE 11

Using the procedure described in Example 9, but starting with 3-{2-[4-(3,4-dimethoxyphenyl)-1-piperazinyl]ethyl}-2-trifluoroacetylimino-6-trifluoromethoxybenzothiazoline hydrochloride (1.4 g) in methanol (30 cc) and a 7% strength aqueous-alcoholic solution (19 cc) of potassium carbonate, 2-imino-3-{2-[4-(3,4-dimethoxyphenyl)-1-piperazinyl]ethyl}-6-trifluoromethoxybenzothiazoline trihydrochloride (0.97 g), m.p. 250° C., is obtained.

3-{2-[4-(3,4-dimethoxyphenyl)-1-piperazinyl]ethyl}-2-trifluoroacetylimino-6-trifluoromethoxybenzothiazoline hydrochloride may be prepared in the following manner: the procedure is as in Example 9, starting with 2-(2-trifluoroacetylimino-6-trifluoromethoxy-3-benzothiazolinyl)ethyl methanesulphonate (4.3 g), toluene (70 cc) and the base liberated from 4-(3,4-dimethoxyphenyl)piperazine dihydrochloride (14 g). The expected hydrochloride (1.45 g), m.p. 260° C., is obtained.

EXAMPLE 12

Using the procedure described in Example 9, but starting with 3-{2-[4-(4-fluorophenyl)-1-piperazinyl]ethyl}-2-trifluoroacetylimino-6-trifluoromethoxybenzothiazoline hydrochloride (1.7 g), methanol (36 cc) and a 7% strength aqueous-methanolic solution (21 cc) of potassium carbonate, 3-{2-[4-(4-fluorophenyl)-1-piperazinyl]ethyl}-2-imino-6-trifluoromethoxybenzothiazoline dihydrochloride, m.p. 260° C., is obtained.

3-{2-[4-(4-fluorophenyl)-1-piperazinyl]ethyl}-2-trifluoroacetylimino-6-trifluoromethoxybenzothiazoline hydrochloride may be prepared in the following manner: the procedure is as in Example 9, starting with 4-(4-fluorophenyl)piperazine (9 g), toluene (70 cc) and 2-(2-trifluoroacetylimino-6-trifluoromethoxy-3-benzothiazolinyl)ethyl methanesulphonate (4.52 g). The expected product (1.7 g), m.p. 240° C., is obtained.

EXAMPLE 13

Using the procedure described in Example 9, but starting with 3-{2-[4-(4-chlorophenyl)-1-piperazinyl]ethyl}-2-trifluoroacetylimino-6-trifluoromethoxybenzothiazoline (1.40 g), methanol (30 cc) and a 7% strength aqueous-methanolic solution (19 cc) of potassium carbonate, 3-{2-[4-(4-chlorophenyl)-1-piperazinyl]ethyl}-2-imino-6-trifluoromethoxybenzothiazoline dihydrochloride (0.9 g), m.p. 270° C., is obtained.

3-{2-[4-(4-Chlorophenyl)-1-piperazinyl]ethyl}-2-trifluoroacetylimino-6-trifluoromethoxybenzothiazoline may be prepared in the following manner: a mixture of 2-(2-trifluoroacetylimino-6-trifluoromethoxy-3-benzothiazolinyl)ethyl methanesulphonate (4.52 g), toluene (70 cc) and the base liberated from 4-(4-chlorophenyl)-piperazine dihydrochloride (13.45 g) is heated to reflux for 1 hour 15 minutes. After cooling to 10° C. and draining of the precipitate, the toluene filtrate is concentrated and then purified by chromatography on a silica column with a mixture of cyclohexane and ethyl acetate (50:50 by volume) as eluent. After recrystallization in ethanol (50 cc), the expected product (1.4 g), m.p. 165° C., is obtained.

EXAMPLE 14

4-Phenyl-1-[2-(4-trifluoromethoxyanilino)ethyl]-piperidine (3.0 g) and potassium thiocyanate (3.2 g) in acetic acid (25 cc) are treated dropwise with bromine (1.3 g) dissolved in acetic acid (15 cc) at a temperature in the region of 20° C. Reaction is continued for 18 hours at this temperature. After the addition of distilled water (100 cc), the reaction medium is neutralized with 30% strength sodium hydroxide and the organic phase is extracted with ethyl acetate (3×50 cc), dried over magnesium sulphate and concentrated to dryness under reduced pressure (20 mmHg; 2,7 kPa). The residue obtained is purified by chromatography on a silica column with ethyl acetate as eluent. After formation of the dihydrochloride by adding 4.2N ethereal hydrogen chloride (4 cc) in ethyl acetate (30 cc), 2-imino-3-[2-(4-phenylpiperidino)ethyl]-6-trifluoromethoxybenzothiazoline dihydrochloride (2.4 g), subliming at about 220° C., is obtained.

4-Phenyl-1-[2-(4-trifluoromethoxyanilino)ethyl]-piperidine may be prepared in the following manner: a mixture of N-(p-toluenesulphonyl)-2-(4-trifluoromethoxyanilino)ethyl p-toluenesulphonate (7.2 g), 4-phenylpiperidine (4.9 g) and sodium hydrogen carbonate (2.4 g) in dimethylformamide (50 cc) is heated to 80° C. for 18 hours. After cooling to a temperature in the region of 20° C., the reaction medium is concentrated to dryness under reduced pressure (7 mmHg; 0.95 kPa). The residue is washed with water (2×30 cc), then taken up with ethanol (50 cc) and concentrated to dryness under reduced pressure. The crude product is treated with 37% strength hydrochloric acid (30 cc) in a mixture of acetic acid (30 cc) and distilled water (20 cc). The mixture is heated to boiling for 3 hours. After cooling to a temperature in the region of 20° C. and the addition of distilled water (100 cc), the aqueous solution is neutralized with 30% strength sodium hydroxide and the organic phase extracted with ethyl acetate. 4-Phenyl-1-[2-(4-trifluoromethoxyanilino)ethyl]piperidine (4.0 g) is obtained in the form of a brown oil, which is used in the crude state in the following reaction.

N-(p-Toluenesulphonyl)-2-(4-trifluoromethoxyanilino)ethyl p-toluenesulphonate may be prepared according to the following process: p-toluenesulphonyl chloride (8.6 g) is added gradually to 2-(4-trifluoromethoxyanilino)ethanol (5.0 g) and triethylamine (6.35 cc) in dichloromethane (50 cc) at 0° C. Reaction is continued for 2 hours at a temperature in the region of 20° C., the reaction medium then washed with distilled water (3×50 cc) and the organic phase dried over magnesium sulphate and concentrated to dryness under reduced pressure (20 mmHg; 2.7 kPa). After the addition of absolute ethanol (50 cc), the precipitate formed is filtered off. N-(p-Toluenesulphonyl)-2-(4-trifluoromethoxyanilino)ethyl p-toluenesulphonate (7.3 g), m.p. 88° C., is obtained.

2-(4-Trifluoromethoxyanilino)ethanol may be prepared in the following manner: 4-trifluoromethoxyaniline (88.5 g) and 2-bromoethanol (31.2 g) are heated to 160° C. for 1.5 hours. After cooling to a temperature in the region of 20° C., the reaction medium is taken up in dichloromethane (200 cc), the insoluble matter filtered off and the filtrate concentrated to dryness under reduced pressure. After purification by chromatography on a silica column with a mixture of ethyl acetate and cyclohexane (40:60 by volume) as eluent, 2-(4-trifluoromethoxyanilino)ethanol (26.8 g) is obtained in the form of an orange-coloured oil.

EXAMPLE 15

The procedure is as in Example 1, but starting with 3-{2-[4-(2-fluorophenyl)-1-piperazinyl]ethyl}-2-trifluoroacetylimino-6-trifluoromethoxybenzothiazoline (0.6 g), methanol (20 cc) and a 7% strength aqueous-alcoholic solution (10 cc) of potassium carbonate. After the addition of 4.2N ethereal hydrogen chloride, 2-imino-3-{2-[4-(2-fluorophenyl)-1-piperazinyl]ethyl}-6-trifluoromethoxybenzothiazoline dihydrochloride (0.335 g), m.p. about 260° C., is obtained.

3-{2-[4-(2-Fluorophenyl)-1-piperazinyl]ethyl}-2-trifluoroacetylimino-6-trifluoromethoxybenzothiazoline may be prepared in the following manner: the procedure is as in Example 1 for the preparation of 3-{2-[4-(2-pyridyl)-1-piperazinyl]ethyl}-2-trifluoroacetylimino-6-trifluoromethoxybenzothiazoline, starting with 2-(2-trifluoroacetylimino-6-trifluoromethoxy-3-benzothiazolinyl)ethyl methanesulphonate (4.52 g ) in toluene (70 cc) and 4-(2-fluorophenyl)piperazine (9g). After purification by chromatography on a silica column with ethyl acetate as eluent, 3-{2-[4-(2-fluorophenyl)-1-piperazinyl]ethyl}-2-trifluoroacetylimino-6-trifluoromethoxybenzothiazoline (0.6 g), is obtained.

EXAMPLE 16

The procedure is as in Example 1, starting with 2-(2-trifluoroacetylimino-6-trifluoromethoxy-3-benzothiazolinyl)ethyl methanesulphonate (4.52 g) in toluene (120 cc) and 4-(3-chlorophenyl)piperazine (7.8 g). After 2 hours under reflux, the toluene filtrate is evaporated under reduced pressure, and methanol (100 cc) and a 7% strength aqueous-alcoholic solution (10 cc) of potassium carbonate are added to the toluene residue. The mixture is stirred at approximately 20° C. The methanol is evaporated off under reduced pressure and the residue is purified by chromatography on a silica column with a mixture of dichloromethane and methanol (95:5 by volume) as eluent, and then with ethyl acetate as eluent. After the addition of 4.2N ethereal hydrogen chloride, 2-imino-3-{2-[4-(3-chlorophenyl)-1-piperazinyl]ethyl}-6-trifluoromethoxybenzothiazoline trihydrochloride (0.9 g), m.p. about 260° C., is obtained.

EXAMPLE 17

The procedure is as in Example 1, starting with 2-(2-trifluoroacetylimino-6-trifluoromethoxy-3-benzothiazolinyl)ethyl methanesulphonate (4.52 g) in toluene (120 cc) and 4-(3-fluorophenyl)piperazine (6.7 g). After 2 hours under reflux, the toluene filtrate is evaporated under reduced pressure, and methanol (100 cc) and a 7% strength aqueous-alcoholic solution (20 cc) of potassium carbonate are added to the toluene residue. After 2 hours' stirring at approximately 20° C., the methanol is evaporated off under reduced pressure and the residue is purified by chromatography on a silica column with a mixture of dichloromethane and methanol (98:2 by volume) as eluent, followed by ethyl acetate. After the addition of 4.2N ethereal hydrogen chloride, 2-imino-3-{2-[4-(3-fluorophenyl)-1-piperazinyl]ethyl}-6-trifluoromethoxybenzothiazoline dihydrochloride (1 g), m.p. about 270° C., is obtained.

EXAMPLE 18

The procedure is as in Example 1, but starting with 3-{2-[4-(2-methoxyphenyl)-1-piperazinyl]ethyl}-2-trifluoroacetylimino-6-trifluoromethoxybenzothiazoline hydrochloride (1.8 g) in methanol (39 cc) and a 7% strength aqueous-alcoholic solution (23 cc) of potassium carbonate. After purification by chromatography on a silica column with acetone as eluent, followed by the addition of 4.2N ethereal hydrogen chloride, 2-imino-3-{2-[4-(2-methoxyphenyl)-1-piperazinyl]ethyl}-6-trifluoromethoxybenzothiazoline trihydrochloride (1.2 g), m.p. 210° C., is obtained.

3-{2-[4-(2-Methoxyphenyl)-1-piperazinyl]ethyl}-2-trifluoroacetylimino-6-trifluoromethoxybenzothiazoline hydrochloride may be prepared in the following manner: the procedure is as in Example 1, starting with 2-(2-trifluoroacetylimino-6-trifluoromethoxy-3-benzothiazolinyl)ethyl methanesulphonate (4.52 g) in toluene (120 cc) and 4-(2-methoxyphenyl)piperazine (7.7 g). After the addition of 4.2N ethereal hydrogen chloride, 3-{2-[4-(2-methoxyphenyl)-1-piperazinyl]-ethyl}-2-trifluoro-acetylimino-6-trifluoromethoxybenzothiazoline hydrochloride (1.8 g), m.p. 230° C., is obtained.

EXAMPLE 19

3-{2-(4-phenyl-1-piperazinyl)ethyl}-2-trifluoroacetylimino-6-trifluoromethylbenzothiazoline (1 g), dissolved in a mixture of 7% strength aqueous potassium carbonate solution (5 cc) and methanol (50 cc), is stirred at a temperature in the region of 20° C. for 3 hours. The medium is concentrated under reduced pressure (20 mmHg, 2.7 kPa) and the residue is taken up in diethylether. The precipitate formed is filtered off and the filtrate is concentrated under reduced pressure. After purification by chromatography on a silica column with ethyl acetate as eluent, followed by the addition of ethereal hydrogen chloride, 2-imino-3-{2-(4-phenyl-1-piperazinyl)ethyl}-6-trifluoromethylbenzothiazoline dihydrochloride (0.5 g), m.p. 260° C. is obtained.

3-{2-(4-phenyl-1-piperazinyl)ethyl}-2-trifluoroacetylimino-6-trifluoromethylbenzothiazoline may be prepared in the following manner: the procedure is as in example 6, starting with 2-(2-trifluoroacetylimino-6-trifluoromethyl-3-benzothiazolinyl)ethyl R-toluenesulfonate (3.5 g) in dimethylformamide (50 cc), sodium hydrogen carbonate (0.6 g), N-phenylpiperazine (1.2 g) and dimethyl formamide (10 cc) for 20 hours at 50° C. After purification by chromatography on a silica column with an ethyl acetate/cyclohexane mixture (30:70 by volume) as eluent, 3-{2-(4-phenyl-1-piperazinyl)ethyl}-2-trifluoroacetylimino-6-trifluoromethylbenzothiazoline is obtained.

2-(2-trifluoroacetylimino-6-trifluoromethyl-3-benzothiazolinyl)ethyl p-toluenesulfonate may be prepared in the following manner: the procedure is as in example 6 starting with 2-(2-trifluoroacetylimino-6-trifluoromethyl-3-benzothiazolinyl)ethanol (5.3 g), pyridine (50 cc) and p-toluenesulphonyl chloride (5.7 g) for 2 hours at 20° C. 2-(2-trifluoroacetylimino-6-trifluoromethyl-3-benzothiazolinyl)ethyl p-toluenesulfonate (7.2 g), m.p. 163° C. is obtained.

2-(2-trifluoroacetylimino-6-trifluoromethyl-3-benzothiazolinyl)ethanol may be prepared in the following manner: the procedure is as in example 6, starting with 2-(2-imino-6-trifluoromethyl-3-benzothiazolinyl)ethanol bromhydrate (10.5 g), ethanol (50 cc), triethylamine (9.5 cc) and ethyl trifluoroacetate (5.2 g). 2-(2-trifluoroacetylimino-6-trifluoromethyl-3-benzothiazolinyl)ethanol (6.55 g) m.p. 198° C. is obtained.

2-(2-imino-6-trifluoromethyl-3-benzothiazolinyl)ethanol bromhydrate may be prepared in the following manner: the procedure is as in the example 6, starting with 2-amino-6-trifluoromethylbenzothiazole (17.9 g), ethanol (50 cc) and 2-bromoethanol. 2-(2-imino-6-trifluoromethyl-3-benzothiazolinyl)ethanol bromhydrate (10.5 g) is obtained.

2-amino-6-trifluoromethylbenzothiazole may be prepared according to the method described in U.S. Pat. No. 2,822,359.

EXAMPLE 20

Using the procedure described in example 19 but starting with 3-{2-[4-(4-fluorophenyl)-1-piperazinyl]ethyl}-2-trifluoroacetylimino-6-trifluoromethylbenzothiazoline (3.5 g), a 7% strength aqueous alcoholic solution (15 cc) of potassium carbonate and methanol (150 cc). 2-imino-3-{2-[4-(4-fluorophenyl)-1-piperazinyl]ethyl}-6-trifluoromethylbenzothiazoline (2.2 g) m.p. 250° C. is obtained.

3-{2-[4-(4-fluorophenyl)-1-piperazinyl]ethyl}-2-trifluoroacetylimino-6-trifluoromethylbenzothiazoline may be prepared in the following manner: the procedure is as in example 6, starting with 2-(2-trifluoroacetylimino-6-trifluoromethyl-3-benzothiazolinyl)ethyl (8.7 g), N-(4-fluorophenyl)piperazine (3.2 g), sodium hydrogenocarbonate (1.43 g) and dimethylformamide (125 cc). 3-{2[4-(4-fluorophenyl)-1-piperazinyl]ethyl}-2-trifluoroacetylimino-6-trifluoromethylbenzothiazoline (3.5 g) is obtained.

EXAMPLE 21

Using the procedure described in Example 19, but starting with 3-{2-[4-(4-methoxyphenyl)-1-piperazinyl]ethyl}-2-trifluoroacetylimino-6-trifluoromethylbenzothiazoline (0.1 g), a 7% strength aqueous solution (0.5 cc) of potassium carbonate and methanol (5 cc). 2-imino-3-{2-[4-(4-methoxyphenyl)-1-piperazinyl]ethyl}-6-trifluoromethylbenzothiazoline (0.095 g) m.p. 270° C. is obtained.

3-{2-[4-(4-methoxyphenyl)-1-piperazinyl]ethyl}-2-trifluoroacetylimino-6-trifluoromethylbenzothiazoline may be prepared in the following manner: the procedure is as in example 6, starting with 2-(2-trifluoroacetylimino-6-trifluoromethyl-3-benzothiazonyl)ethyl p-toluene sulphonate (3.5 g), N-(4-methoxyphenyl)piperazine dihydrochloride (1.9 g), sodium hydrogenocarbonate (1.2 g) and dimethylformamide (60 cc). 3-{2-[4-(4-methoxyphenyl)-1-piperazinyl]ethyl}-2-trifluoroacetylimino-6-trifluoromethylbenzothiazoline (0.1 g) m.p. 120° C. is obtained.

The present invention also relates to medicinal products consisting of a compound of formula (I), or a salt of such a compound, in the pure state or in the form of a composition in which it is combined with any other pharmaceutically compatible product, which can be inert or physiologically active. The medicinal products according to the invention may be employed orally, parenterally, rectally or topically.

As solid compositions for oral administration, tablets, pills, powders (gelatin capsules, wafer capsules) or granules may be used. In these compositions, the active principle according to the invention is mixed with one or more inert diluents such as starch, cellulose, sucrose, lactose or silica.

These compositions can also comprise substances other than diluents, e.g. one or more lubricants such as magnesium stearate or talc, a coloring, a coating (dragees) or a varnish.

As liquid compositions for oral administration, solutions, suspensions, emulsions, syrups and elixirs of a pharmaceutically acceptable nature, containing inert diluents such as water, ethanol, glycerol, vegetable oils or liquid paraffin, may be used. These compositions can comprise substances other than diluents, e.g. wetting products, sweeteners, thickeners, flavourings or stabilizers.

The sterile compositions for parenteral administration can preferably be solutions, aqueous or non-aqueous, suspensions or emulsions. As a solvent or vehicle, water, propylene glycol, a polyethylene glycol, vegetable oils, especially olive oil, injectable organic esters, e.g. ethyl oleate, or other suitable organic solvents may be employed. These compositions can also contain adjuvants, especially wetting agents, tonicity regulators, emulsifiers, dispersants and stabilizers. The sterilization may be carried out in several ways, e.g. by aseptic filtration, by incorporating sterilizing agents in the composition, by irradiation or by heating. They may also be prepared in the form of sterile solid compositions which can be dissolved at the time of use in sterile distilled water or any other sterile injectable medium.

The compositions for rectal administration are suppositories or rectal capsules which contain, apart from the active product, excipients such as cocoa butter, semi-synthetic glycerides or polyethylene glycols.

The compositions for topical administration can be, e.g., creams, ointments, lotions, eye washes, mouth washes, nasal drops or aerosols.

In human therapy, the compounds according to the invention are especially useful in the treatment and prevention of convulsive phenomena, schizophrenic disorders, and in particular the deficiency forms of schizophrenia, sleep disorders, phenomena linked to cerebral ischaemia and also neurological conditions in which glutamate may be implicated, such as Alzheimer's disease, Huntington's chorea, amyotrophic lateral sclerosis and olivopontocerebella atrophy.

The doses depend on the effect sought, the treatment period and the administration route used; they are generally between 30 and 300 mg per day in oral administration for an adult, with unit doses ranging from 10 to 100 mg of active substance.

Generally speaking, the doctor will determine the appropriate dosage in accordance with the age and weight and all other factors characteristic of the subject to be treated.

The examples which follow illustrate some compositions according to the invention.

EXAMPLE A

Hard gelatin capsules containing 50 mg of active product and having the following composition are prepared according to the usual technique:

| | |
|---|---|
| 2-Imino-3-{2-[4-(2-pyridyl)-1-piperazinyl]ethyl}-6-trifluoromethoxybenzothiazoline | 50 mg |
| Cellulose | 18 mg |
| Lactose | 55 mg |
| Colloidal silica | 1 mg |
| Carboxymethylstarch sodium | 10 mg |
| Talc | 10 mg |

EXAMPLE B

Tablets containing 50 mg of active product and having the following composition are prepared according to the usual technique:

| | |
|---|---|
| 2-Imino-3-{2-[4-(4-methylphenyl)-1-piperazinyl]ethyl}-6-trifluoromethoxybenzothiazoline | 50 mg |
| Lactose | 104 mg |
| Cellulose | 40 mg |
| Polyvidone | 10 mg |
| Carboxymethylstarch sodium | 22 mg |
| Talc | 10 mg |
| Magnesium stearate | 2 mg |
| Colloidal silica | 2 mg |
| Mixture of hydroxymethylcellulose, glycerol and titanium oxide (71:3.5:24.5) | q.s. 1 finished film-coated tablet weighing 245 mg |

EXAMPLE C

An injectable solution containing 10 mg of active product having the following composition is prepared:

| | | |
|---|---|---|
| 3-[2-(4-Benzyl-1-piperazinyl)ethyl]-2-imino-6-trifluoromethoxybenzothiazoline | | 10 mg |
| Benzoic acid | | 80 mg |
| Benzyl alcohol | | 0.06 cc |
| Sodium benzoate | | 80 mg |
| Ethanol, 95% strength | | 0.4 cc |
| Sodium hydroxide | | 24 mg |
| Propylene glycol | | 1.6 cc |
| Water | q.s. | 4 cc |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A compound of formula:

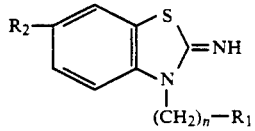

in which $R_1$ represents a 1-piperazinyl radical substituted at the 4-position with (a) a phenyl radical, (b) a phenyl radical substituted with at least one substituent selected from halogen atoms and alkyl and alkoxy radicals, (c) a phenylalkyl radical, (d) a pyridyl radical or (e) a pyrimidinyl radical;

a 1,2,3,6-tetrahydro-1-pyridyl radical substituted at the 4-position with a phenyl radical or a phenyl radical substituted with at least one substituent selected from halogen atoms and alkyl and alkoxy radicals, a piperidino radical substituted at the 4-position with a phenyl radical or a phenyl radical substituted with at least one substituent selected from halogen atoms and alkyl and alkoxy radicals, $R_2$ represents a polyfluoroalkoxy or polyfluoroalkyl radical, and n is equal to 2 or 3, on the understanding that the alkyl and alkoxy radicals and the alkyl and alkoxy portions contain 1 to 4 carbon atoms in a straight or branched chain, as well as its salts with an inorganic or organic acid.

2. A compound of formula (I) according to claim 1 for which $R_2$ represents a trifluoromethoxy, pentafluoroethoxy, 2,2,2-trifluoroethoxy, 1,1,2,2-tetrafluoroethoxy or trifluoromethyl radical.

3. 3-{2-(4-4-fluorophenyl)-1-piperazinyl)ethyl}-2-imino-6-trifluoromethoxybenzothiazoline and its salts with organic or inorganic acids.

4. 2-imino-3-(2-(4-phenylpiperazinyl)ethyl)-6-trifluoromethoxybenzothiazoline and its salts with organic or inorganic acids.

5. A pharmaceutical composition which comprises, as active principle, a pharmaceutically effective amount of at least one compound according to claim 1 or a pharmaceutically acceptable salt of such compound with an inorganic or organic acid, in association with a compatible pharmaceutically acceptable carrier.

6. A pharmaceutical composition which comprises, as active principle, a pharmaceutically effective amount of at least one compound according to claim 2 or a pharmaceutically acceptable salt of such compound with an inorganic or organic acid, in association with a compatible pharmaceutically acceptable carrier.

7. A pharmaceutical composition which comprises, as active principle, a pharmaceutically effective amount of compound according to claim 3 or a pharmaceutically acceptable salt of such compound with an inorganic or organic acid, in association with a compatible pharmaceutically acceptable carrier.

8. A pharmaceutical composition which comprises, as active principle, a pharmaceutically effective amount of compound according to claim 4 or a pharmaceutically acceptable salt of such compound with an inorganic or organic acid, in association with a compatible pharmaceutically acceptable carrier.

9. A method for the inhibition of glutamate activity which comprises administering to a subject in need of such treatment an effective amount of a compound of formula (I) as defined in claim 1.

* * * * *